United States Patent

Ando et al.

Patent Number: 5,879,943
Date of Patent: Mar. 9, 1999

[54] HUMIDITY DETECTION METHOD

[75] Inventors: Masanori Ando; Tetsuhiko Kobayashi; Masatake Haruta, all of Ikeda, Japan

[73] Assignees: Agency of Industrial Science & Technology, Tokyo, Japan; Research Development Corporation, Kawaguchi, Japan

[21] Appl. No.: 872,940

[22] Filed: Jun. 11, 1997

Related U.S. Application Data

[63] Continuation of Ser. No. 526,355, Sep. 12, 1995, abandoned.

[30] Foreign Application Priority Data

Sep. 16, 1994 [JP] Japan ................................ 6-222181

[51] Int. Cl.[6] ..................................................... G01N 33/18
[52] U.S. Cl. ......................... 436/41; 73/29.01; 73/335.01; 73/73; 422/82.05; 422/82.09; 436/39; 436/164
[58] Field of Search ................................ 436/39, 41, 164; 422/82.05, 82.09; 73/73, 29.01, 29.02, 335.01, 29.04, 29.05

[56] References Cited

U.S. PATENT DOCUMENTS

| 4,041,437 | 8/1977 | Matsuura et al. ....................... 436/39 |
|---|---|---|
| 4,050,048 | 9/1977 | Frazee . |
| 4,270,085 | 5/1981 | Terada et al. ........................... 73/336.5 |
| 4,393,434 | 7/1983 | Imai et al. ............................. 73/336.5 |
| 4,419,021 | 12/1983 | Terada et al. ......................... 73/336.5 |
| 4,975,249 | 12/1990 | Elliott ....................................... 436/39 |
| 5,290,516 | 3/1994 | Greco et al. ............................. 436/41 |

FOREIGN PATENT DOCUMENTS

| 55136954 | 10/1980 | Japan . |
|---|---|---|
| 62142564 | 6/1987 | Japan . |
| 345672 | 6/1930 | United Kingdom . |

OTHER PUBLICATIONS

The Merck Index, Tenth Ed., Merck & Co Inc (1983) pp. 810–811.
The Merck Index, Tenth Ed. Merck & Co, Inc (1983) p.579.

*Primary Examiner*—Jan Ludlow
*Attorney, Agent, or Firm*—Sherman and Shalloway

[57] ABSTRACT

A humidity detection material includes oxide of at least one metal selected from the group consisting of Mg, Ca, Mn, Fe, Co, Ni, and Cu. The metal oxide is preferably in the form of a porous material. The metal oxide is formed preferably in the form of a thin film on a transparent substrate. The humidity detection material is contacted with water vapor in the presence of a gas such as air, and the optical absorbance of the humidity detection material is measured to detect the humidity. The humidity can be detected by an optical method.

3 Claims, 2 Drawing Sheets

HUMIDITY DETECTION METHOD

This application is a continuation of application Ser. No. 08/526,355, filed Sep. 12, 1995 now abandoned.

FIELD OF THE INVENTION

This invention relates to a humidity detection material and a humidity detection method using the material

BACKGROUND ART

Detection of moisture in gases such as air, that is, humidity, is important in relation to environmental problems. Recently, not only for obtaining more comfortable life space, but also with the advance in home automation and factory automation, detection, measurement, and control of humidity by a sensor becomes more and more important in view of operation environment of precision devices which are subject to troubles due to dew condensation.

Heretofore, various methods have been used for detecting humidity of gases such as air, such as (1) a method utilizing elongation of hair when it absorbs water vapor (so-called hair hygrometer), (2) a method utilizing a change in electrical resistance of an electrolyte by water vapor, (3) a method of detecting a change in resistance or volume of a dielectric material such as organic substances, semiconductors, metal oxides, and the like when moisture is adsorbed by the material, and (4) a method of detecting a weight change of a quartz oscillator coated with polyamide when moisture is adsorbed by the oscillator.

However, with these conventional methods, the method (1) has problems in that the operable ambient temperature is limited to the vicinity of room temperature, and the method cannot be used in the presence of corrosive vapors such as acid or base. In the electrochemical method (2), the device becomes complex in structure as compared to other methods, and requires maintenance of the electrodes and electrolyte. A method utilizing a change in resistance of the method (3) often uses conductivity of $H^+$ ion generated by adsorption of water, and therefore the resistance of the humidity sensor element becomes excessively high at low humidities where the adsorbed water amount is small, and the resistance and humidity tend to be difficult to be exactly measured by an ordinary method. Further, the device generally has a difficulty of measurement due to high element resistance, and a method using a hydrophilic polymer as a moisture sensitive material cannot be used at high humidities having a possibility of dew condensation.

Further, in the method (4) using a weight change, since a signal is always output when a change in the weight of element occurs even by adsorption of molecules other than water, it requires a devise for selective detection of only water, which is sometimes difficult. Since the humidity detection signal is output as an electrical signal, the humidity detection signal tends to be disturbed by strong electromagnetic waves or noise generated by various emission sources when humidity detection is carried out by a remote control in a wide area such as in a chemical plant or a coal mine. Further, the humidity detection method based on the electrical signal is difficult to be combined directly with an information system or control system using optical signals, which recently becomes widely used, and an apparatus is required for converting the electrical signal to optical signal.

Therefore, development is in demand of a humidity detection apparatus which is immune to electrical disturbance and can be easily combined directly with an optical information system or optical control system. Heretofore, as methods for detecting humidity by an optical signal, (1) a method utilizing humidity dependence of visible light absorption spectrum or fluorescence intensity of a film comprising a polymeric carrier combined with an organic dye such as crystal violet, betaine type dye, or rhodamine type dye, and (2) a method utilizing a change in visible light absorption spectrum of cobalt chloride carried on a polymeric carrier, have been studied. However, organic dyes and organic polymers are low in heat resistance and relatively narrow in the operation temperature range, and tend to undergo an irreversible change if a highly reactive vapor is present in the environment. Therefore, a humidity detection material with improved chemical and thermal stability and a humidity detection method using the material are required.

In view of the above prior art problems, a primary object of the present invention is to provide a humidity detection material which is high in chemical and thermal stability and can detect humidity by an optical means and a humidity detection method using the material.

SUMMARY OF THE INVENTION

The inventors have conducted intensive studies to find a method for detecting humidity of a gas such as air by an optical signal. As a result, they have found that an oxide of Mg, Ca, Mn, Fe, Co, Ni, or Cu varies in optical absorbance in response to the humidity (partial pressure of water vapor) of the environment when contacted with water vapor in a gas such as air, detection of humidity is possible by an optical signal using the characteristics, and accomplished the present invention.

In accordance with the present invention, there is provided a humidity detection material comprising oxide of at least one metal selected from the group consisting of Mg, Ca, Mn, Fe, Co, Ni, and Cu. Further, the present invention provides the humidity detection material in which the metal oxide is a porous material. Further, the present invention provides the humidity detection material comprising the metal oxide formed as a thin film on a transparent substrate. The present invention provides a method for detecting humidity in which the humidity detection material is contacted with a gas containing moisture (water vapor), and an optical absorbance of the humidity detection material at that time is measured to detect the humidity. The gas is not specifically limited, it may be a gas in which water vapor can stably exist at various concentrations, and such a gas includes air, $N_2$, Ar, He, $H_2$, CO, $CO_2$, and mixtures thereof.

The present invention will be described. The humidity detection material of the present invention is at least one metal oxide of Mg, Ca, Mn, Fe, Co, Ni, and Cu. These oxides have a property to vary the optical absorbance when contacting with water vapor in a gas. Moreover, the optical absorbance varies with the water vapor concentration (humidity) in the gas. The reason for such a phenomenon has yet to be elucidated but, for example, in the case of cobalt oxide ($Co_3O_4$), it is estimated as due to the following principle. When cobalt oxide is placed in dry air, and then water vapor is added to the dry air environment, first on the surface of the cobalt oxide, $H_2O$ dissociates to $H^+$ and $OH^-$. The resulting $OH^-$ is chemically combined with the metal ion, and $H^+$ with the oxygen ion, individually forming a surface hydroxy group. At this time, when $H^+$, $OH^-$, or surface hydroxy group further chemically interacts with oxygen anions or gas molecules which are normally adsorbed to the cobalt oxide surface, electrons are removed from the cobalt oxide when the concentration of water vapor is high, and the electron density in the cobalt oxide is decreased, or electrons are pushed back to the cobalt oxide when the water vapor concentration is low, and the electron density in the cobalt oxide is increased.

Optical absorbance of cobalt oxide varies with the electron density, the optical absorbance is decreased when the electron density is high, and the optical absorbance is increased when the electron density is low. As described above, cobalt oxide varies in optical absorbance according to the water vapor concentration (humidity).

The above phenomenon is not seen in all metal oxides, but is seen when the following three conditions are met.

(i) Water molecule is reversibly adsorbed on the surface in equilibrium with water vapor in the gas phase, the adsorbed $H_2O$ dissociates to $H^+$ and $OH^-$ to be reversibly combined with the surface of the metal oxide.

(ii) Electron density of the metal oxide in the gas is varied when $H_2O$, $H^+$, and $OH^-$ are adsorbed.

(iii) Optical absorbance of the metal oxide is varied with a change in electron density. The above-shown oxides of Mg, Ca, Mn, Fe, Co, Ni, and Cu exhibit changes in optical absorbance according to a change in humidity. The metal oxides used in the present invention are not specifically limited in terms of the oxidation state of metal, and oxides of various oxidation states such as MgO, CaO, $MnO_2$, $Mn_3O_4$, $Fe_2O_3$, $Fe_3O_4$, CoO, $Co_3O_4$, NiO, and CuO can be used. Of these oxides, CaO, $Co_3O_4$, NiO, and CuO are particularly preferable. Metal oxides here, in addition to single oxide types, include mixtures of two or more oxides, and composite oxides such as $MnCo_2O_4$, $NiCo_2O_4$, and $NiMnCo_4O_8$. These metal oxides can be prepared by conventional methods known in the art.

The metal oxide used in the present invention may be mixed with a substance in the preparation of the metal oxide, which itself does not exhibit a change in optical absorbance by a change in humidity, but increases a change in the optical absorbance of the metal oxide by a change in humidity to improve the sensitivity. Such a substance includes organic compounds such as camphor ($C_{10}H_{16}O$) and urea ($CO(NH_2)_2$) when the metal oxide is prepared by pyrolysis of a metal salt of organic acid such as cobalt octanoate or a nitrate such as nickel nitrate. Since camphor or urea, which is solid at room temperature, vaporizes by heating, the metal oxide obtained from a metal salt mixed with camphor or urea is porous and has a large surface area compared with a metal oxide obtained without adding the compound, and can adsorb large amounts of water on the surface. Therefore, the thus obtained metal oxide shows a sharp change in optical absorbance with a change in humidity. In this case, the ratio of the number of metal atoms in the raw material compound and the number of molecules of the added substance is normally about (1:0.01) to (1:5).

In the present invention, the form of the metal oxide is not specifically limited, but can be used in various forms such as thin film or powder. For example, in a method in which the optical absorbance is measured by a transmission method which is described later, the metal oxide is normally in the form of a thin film. When the optical absorbance is measured by a diffuse-reflectance method, the metal oxide is normally in the powder form or in the form of a molded pellet.

When, in the present invention, the metal oxide is used in the form of a thin film, a thin film of the metal oxide is formed on a transparent substrate. The transparent substrate is not specifically limited, but glass mainly comprising $SiO_2$, quartz, or sapphire comprising $Al_2O_3$ is normally used. The formation method of the thin film is not specifically limited, but various conventional methods can be applied, vapor phase methods such as sputtering method, vacuum deposition method, and CVD method, and a method in which a solution of metal nitrate, organic acid metal salt, or metal alkoxide is coated on the substrate and then pyrolyzed. The thickness of the thin film is not specifically limited but, since a change in optical absorbance occurs mainly in the vicinity of the surface of the thin film, if the thin film is too thick, the changing rate of optical absorbance is decreased, and the detection sensitivity is decreased. In general, since a uniform and dense thin film such as formed by sputtering is relatively small in the surface area, the thickness is preferably 5 to 20 nm. On the other hand, when the thin film is formed by solution coating and pyrolysis, the resulting thin film has a relatively large surface area, and a change in optical absorbance can be detected even with a thicker film.

Further, when the metal oxide is used in the form of a powder, the powder is preferably in the form of a fine powder with a particle diameter of less than 1 $\mu$m. The fine powdered metal oxide may be molded to a pellet. The metal oxide may be used by mixing with other substances. The substance does not exhibit a change in optical absorbance by a change in humidity, but makes the metal oxide porous or increases the mechanical strength of the oxide. A substance which increases the mechanical strength is silica ($SiO_2$) or alumina ($Al_2O_3$).

The humidity detection material of the present invention varies in optical absorbance according to a change in humidity of a gas. To detect the humidity utilizing this characteristic, it is used as follows. In the humidity detection method according to the present invention, the optical absorbance of the humidity detection material is measured when the humidity detection material contacts with a gas to be detected for humidity. The optical absorbance of the humidity detection material can be measured by a conventional method known in the art. For example, the following known methods are possible: a method of measuring the optical absorbance from the strength of transmission light using the humidity detection material comprising a metal oxide layer in the form of a thin film on a transparent substrate; a method in which, using a pellet-formed metal oxide formed from the powdered metal oxide, reflected light from the pellet is measured by a diffuse-reflectance method to estimate the optical absorbance; a method in which the metal oxide is adhered to the surface of an optical waveguide to measure the optical absorbance; and a method of measuring the optical absorbance utilizing an opto-acoustic effect. Thus, humidity of a gas can be detected or measured by measuring the optical absorbance using the humidity detection material of the present invention.

The optical absorbance can be evaluated according to various conventional criteria such as absorbance or transmittance. Wavelength of light used for measuring the optical absorbance is not specifically limited, but preferably about 300 to 2,500 nm. Measurement of optical absorbance is preferably carried out at a temperature of above 0° C. in order to prevent freezing of water on the surface of the metal oxide which may occur under a high humidity condition. On the other hand, if the optical absorbance is measured at a high temperature of above 500° C., fine particles of the metal oxide comprising the powder or film may agglomerate due to heat resulting in a change in humidity detection characteristics over time. Therefore, the measuring temperature is preferably 1° to 300° C. However, since the optical absorbance of most metal oxides used in the present invention is varied by the presence of a reducing gas such as CO or $H_2$ in the air (see Japanese Patent Laid-open Publication 03-89162), it is necessary to separate the variation of optical absorbance due to a change in humidity from the variation of optical absorbance due to a reducing gas. Therefore, to detect only the humidity variation from the optical absorbance without influence of a reducing gas present in the air, it is more preferable that the measuring temperature is 1° to 150° C.

DETAILED DESCRIPTION OF EXAMPLES AND COMPARATIVE EXAMPLES

The present invention will now be described in detail with reference to the examples.

EXAMPLE 1

A film of a mixture of cobalt octoate and camphor (number of cobalt atoms:number of camphor molecules= 1:1) was formed on a glass substrate (one side) by spin coating, and calcined at 380° C. for 2 hours to obtain a 60 nm thick cobalt oxide ($Co_3O_4$) thin film. The cobalt oxide thin film was maintained at 25° C., and measured for an ultraviolet —visible—near-infrared absorption spectrum of transmission light individually in (a) air containing moisture of 90% relative humidity (RH) and (b) air containing moisture of 10% relative humidity (RH). The ultraviolet—visible—near-infrared absorption spectrum was measured using a spectrophotometer with an optical fiber while flowing the measured air at a rate of 100 ml/min in a quartz cell (volume: 200 ml). The results of measurement are shown in FIG. 1.

Figure 1:
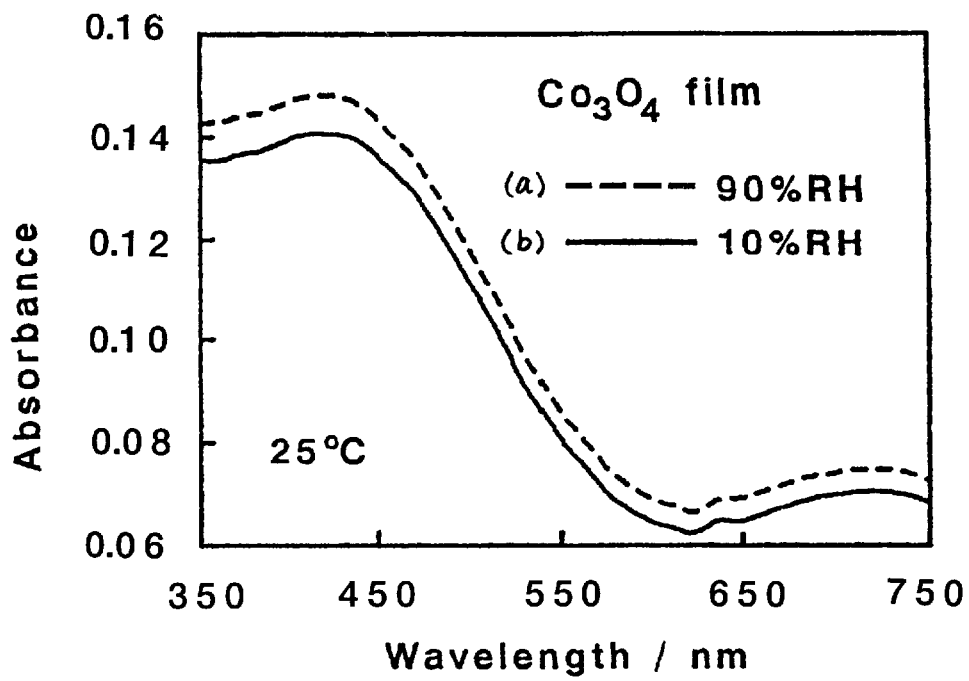
FIG. 1 is a diagram showing an ultraviolet—visible—near-infrared absorption spectrum of a cobalt oxide thin film in high-humidity and low-humidity air.

As can be seen from comparison of the dotted line (a) and the solid line (b) in FIG. 1, optical absorbance of the cobalt oxide thin film varies in a wide wavelength region of ultraviolet—visible—near-infrared light in response to variation of humidity of the air. Therefore, variation of humidity of the air can be detected by measuring the optical absorbance of the cobalt oxide thin film at a single wavelength within the wavelength region. Further, it can also be seen that the absolute change of optical absorbance is the largest in the vicinity of 350 to 400 nm in wavelength.

Figure 2:
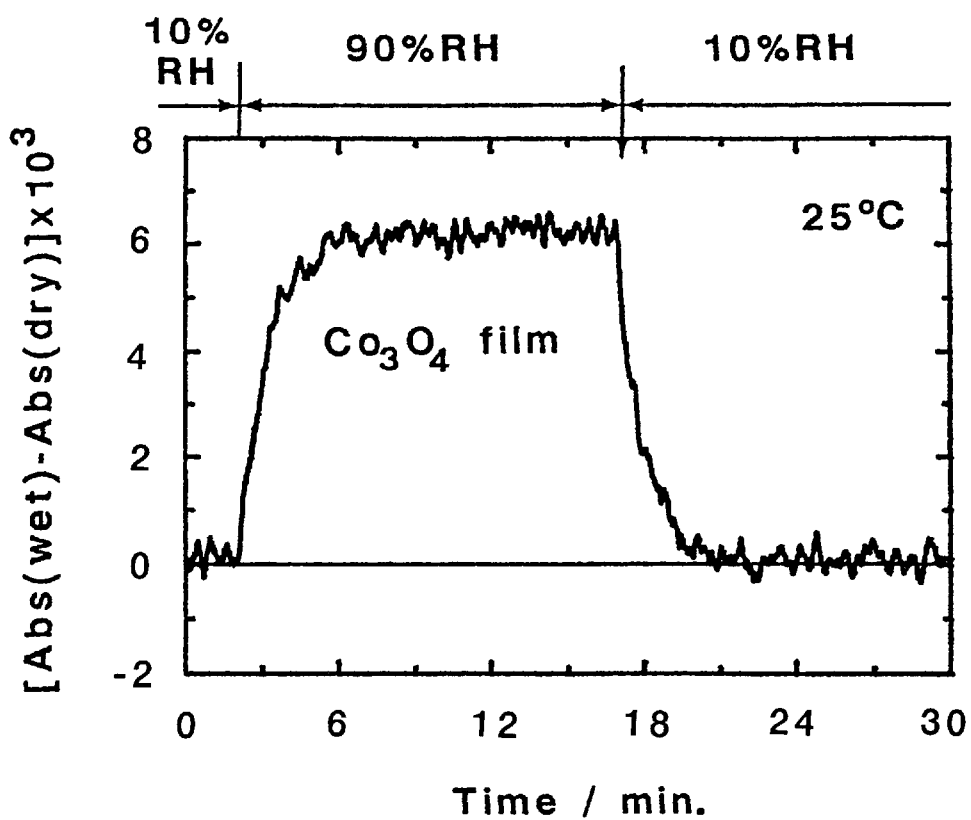
FIG. 2 is a diagram showing a change in optical absorbance of a cobalt oxide thin film with a change in humidity.

Further, the cobalt oxide thin film was maintained at 25° C., the atmosphere was replaced from air containing moisture of 10% relative humidity to air containing moisture of 90% relative humidity, and after 15 minutes, the atmosphere was reverted back to air containing moisture of 10% relative humidity, and optical absorbance of the cobalt oxide thin film to 400 nm wavelength light was measured. The result is shown in FIG. 2. It can be seen that the optical absorbance of the cobalt oxide thin film reversibly varies in response to a change in humidity of air in a response time of within several minutes.

Figure 3:
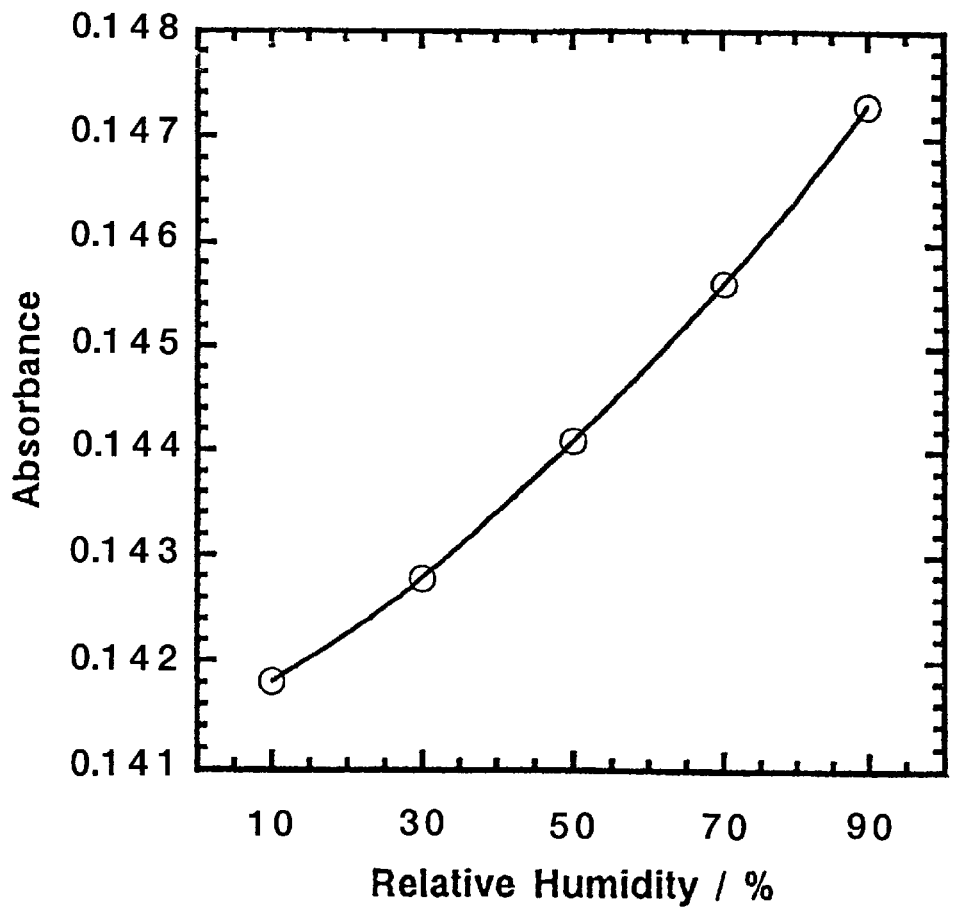
FIG. 3 is a diagram showing the relationship between relative humidity and optical absorbance of a cobalt oxide thin film.

Still further, the cobalt oxide thin film was maintained at 25° C., the atmosphere was replaced to air containing moisture of individually 10%, 30%, 50%, 70%, and 90% relative humidity, and optical absorbance of the cobalt oxide thin film to 400 nm wavelength light was measured. The results are shown in FIG. 3. It can be seen that the optical absorbance varies in response to relative humidity of the air. Therefore, humidity can be measured by contacting the cobalt oxide thin film with water vapor in the presence of air, and measuring the optical absorbance of the cobalt oxide thin film at that time at least to a single wavelength, for example, 400 nm wavelength light. That is, relative humidity at that time can be known by measuring the optical absorbance.

EXAMPLE 2

A nickel octanoate film was formed on a glass substrate (one side) by spin coating, and calcined at 380° C. for 2 hours to obtain a 70 nm thick nickel oxide (NiO) thin film. The nickel oxide thin film was maintained at 15° C., and measured for an ultraviolet—visible—near-infrared absorption spectrum of transmission light individually in (a) air containing moisture of 95% relative humidity and (b) air containing moisture of 5% relative humidity. The results are shown in FIG. 4.

Figure 4:
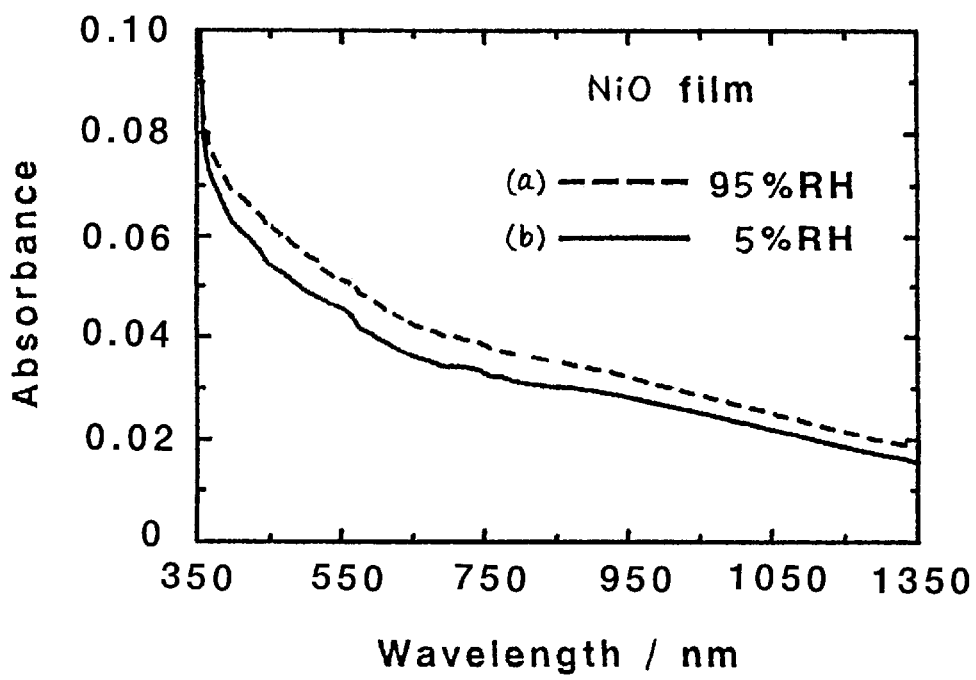
FIG. 4 is a diagram showing an ultraviolet—visible—near-infrared absorption spectrum of a nickel oxide thin film in high-humidity and low-humidity air.

As can be seen from comparison of the dotted line (a) and the solid line (b) in FIG. 4. optical absorbance of the nickel oxide thin film varies in a wide wavelength region of ultraviolet—visible—near-infrared light in response to variation of humidity of the air. Therefore, variation of humidity of the air can be detected by measuring the optical absorbance of the nickel oxide thin film at a single wavelength within the wavelength region. Further, it can also be seen that the absolute change of optical absorbance is almost constant in the range of 350 to 1350 nm in wavelength.

EXAMPLE 3

A 10 nm thick copper oxide (CuO) thin film was formed on a glass substrate (one side) by sputtering. The copper oxide thin film was maintained at 18° C., and measured for an optical absorbance to 400 nm wavelength light individually in (a) air containing moisture of 95% relative humidity and (b) air containing moisture of 5% relative humidity. As a result, optical absorbance of the copper oxide thin film in the individual atmospheric air of (a) and (b) was 0.125 and 0.121, respectively.

This shows that the optical absorbance of the copper oxide thin film in the visible light region varies in response to variation of humidity of air.

EXAMPLE 4

A magnesium naphthenate film was formed on a glass substrate (one side) by spin coating, and calcined at 380° C. for 2 hours to obtain a magnesium oxide (MgO) thin film. The magnesium oxide thin film was maintained at 20° C., and measured for an optical absorbance to 900 nm wavelength light individually in (a) air containing moisture of 80% relative humidity and (b) air containing moisture of 5% relative humidity. As a result, optical absorbance of the magnesium oxide thin film was 0.012 and 0.006, respectively.

EXAMPLE 5

A calcium octanoate film was formed on a glass substrate (one side) by spin coating, and calcined at 380° C. for 2 hours to obtain a calcium oxide (CaO) thin film. The calcium oxide thin film was maintained at 14° C., and measured for an optical absorbance to 400 nm wavelength light individually in (a) air containing moisture of 80% relative humidity and (b) air containing moisture of 5% relative humidity. As a result, optical absorbance of the calcium oxide thin film was 0.036 and 0.032, respectively.

EXAMPLE 6

An iron octanoate film was formed on a glass substrate (one side) by spin coating, and calcined at 380° C for 2 hours to obtain a 25 nm thick iron oxide ($Fe_2O_3$) thin film. The iron oxide thin film was maintained at 28° C., and measured for an optical absorbance to 400 nm wavelength light individually in (a) air containing moisture of 70% relative humidity and (b) air containing moisture of 5% relative humidity. As a result, optical absorbance of the iron oxide thin film was 0.220 and 0.206, respectively.

EXAMPLE 7

A manganese octanoate film was formed on a glass substrate (one side) by spin coating, and fired at 380° C. for 2 hours to obtain a 32 nm thick manganese oxide ($Mn_3O_4$) thin film. The manganese oxide thin film was maintained at 28° C., and measured for an optical absorbance to 400 nm wavelength light individually in (a) air containing moisture of 70% relative humidity and (b) air containing moisture of 5% relative humidity. As a result, optical absorbance of the manganese oxide thin film was 0.103 and 0.099, respectively.

The humidity detection material of the present invention is superior in chemical and thermal stability. Therefore, a humidity sensor having higher chemical and thermal stability than humidity detection materials using conventional organic polymer materials can be formed, and the sensor can be used in wider conditions. Further, since, with the humidity detection material of the present invention, humidity of a gas can be detected by an optical means, that is, by an optical signal, the material can be combined directly with an information system or control system using an optical signal which recently has become practically used. Further, humidity can be detected and measured more easily by contacting the humidity detection material of the present invention with a gas containing moisture and measuring the optical absorbance at that time of the humidity detection material.

What is claimed is:

1. A humidity detection method comprising:

contacting an oxide of at least one metal selected from the group consisting of Mn, Co, Ni, and Cu with a moisture-containing gas, and measuring an optical absorbance of said oxide, wherein the optical absorbance varies with the humidity.

2. A humidity detection method comprising: contacting a porous oxide of at least one metal selected from the group consisting of Mn, Co, Ni, and Cu with a moisture-containing gas, and measuring an optical absorbance of said oxide, wherein the optical absorbance varies with the humidity.

3. A humidity detection method comprising:

contacting a transparent substrate with an oxide thin film of at least one metal selected from the group consisting of Mn, Co, Ni, and Cu formed thereon with a moisture-containing gas, and measuring an optical absorbance of said oxide at that oxide, wherein the optical absorbance varies with the humidity.

* * * * *